US012805657B1

(12) United States Patent
Libolt

(10) Patent No.: US 12,805,657 B1
(45) Date of Patent: Nov. 24, 2026

(54) METHOD OF MANUFACTURING AND USING A PELVIC PILLOW TO ALLEVIATE PRESSURE ON A PERSONS SACRUM

(71) Applicant: Erica Libolt, New Paltz, NY (US)

(72) Inventor: Erica Libolt, New Paltz, NY (US)

( * ) Notice: Subject to any disclaimer, the term of this patent is extended or adjusted under 35 U.S.C. 154(b) by 0 days.

(21) Appl. No.: 19/305,931

(22) Filed: Aug. 21, 2025

(51) Int. Cl.
*A47G 9/10* (2006.01)
*A61F 5/01* (2006.01)
*B29C 33/38* (2006.01)
*B29C 33/40* (2006.01)
*G06T 17/00* (2006.01)

(52) U.S. Cl.
CPC .................. *A47G 9/10* (2013.01); *A61F 5/01* (2013.01); *B29C 33/3842* (2013.01); *B29C 33/40* (2013.01); *G06T 17/00* (2013.01); *A47G 2009/1018* (2013.01); *B29K 2861/04* (2013.01)

(58) Field of Classification Search
None
See application file for complete search history.

(56) References Cited

U.S. PATENT DOCUMENTS 3,757,364 A * 9/1973 Downing ................. A47G 9/10 5/636
4,132,228 A * 1/1979 Green .................... A47C 7/029 297/284.3
4,454,090 A * 6/1984 Saumell ................. B29D 12/02 264/222
4,470,782 A * 9/1984 Zimmerman, Jr. ...... A43B 7/28 264/223
4,635,306 A * 1/1987 Willey ................. A47C 16/005 D6/601
4,736,477 A * 4/1988 Moore ................. A47C 20/021 128/892
4,756,090 A * 7/1988 Pedrow .................... A47G 9/10 5/636
4,828,325 A * 5/1989 Brooks ............... B29C 44/1204 264/45.2
4,890,235 A * 12/1989 Reger .................. A61G 5/1043 264/222
4,912,788 A * 4/1990 Lonardo ............ A61G 7/05723 297/230.13
4,951,336 A * 8/1990 Silverman ............ A61G 5/1043 297/DIG. 6
4,972,351 A * 11/1990 Reger ....................... A61F 5/01 264/222

(Continued)

*Primary Examiner* — Emmanuel S Luk
(74) *Attorney, Agent, or Firm* — Dale J. Ream

(57) ABSTRACT

A method for alleviating pressure on a person's sacrum involves providing a pelvic pillow that is customized to the sacrum of the person using it. The pelvic pillow includes at an inclined upper surface configured to elevate the patient's pelvis to a predetermined angle, the inclined surface having a thicker end that, in use, is positioned toward the patient's feet and a thinner end positioned toward the patient's head. The method includes steps for customizing the pelvic pillow to a respective user, including providing a moldable material to the user with instructions for the patient to apply pressure to the moldable material while lying in a supine position so as to create a mold representing the sacral region of the user's body. The method includes scanning the mold to generate a digital file representative of the sacral contour and then fabricating the pelvic pillow from a foam material.

12 Claims, 6 Drawing Sheets

(56) References Cited

U.S. PATENT DOCUMENTS

| | | | | | |
|---|---|---|---|---|---|
| 5,027,461 | A * | 7/1991 | Cumberland | A61B 5/1074 | 264/223 |
| 5,070,865 | A * | 12/1991 | Iams | A47G 9/1009 | 606/240 |
| 5,470,590 | A * | 11/1995 | Brubaker | A47C 23/002 | 264/222 |
| 5,746,952 | A * | 5/1998 | Marshall | B29D 35/122 | 264/40.1 |
| 6,284,168 | B1 * | 9/2001 | Robinson | B29C 33/3842 | 264/130 |
| 7,552,494 | B2 * | 6/2009 | Peterson | A43D 1/02 | 33/3 R |
| 7,918,510 | B2 * | 4/2011 | van den Nieuwboer | A61G 5/12 | 297/440.14 |
| 8,014,001 | B2 * | 9/2011 | Trenkenschu | G01B 11/24 | 356/608 |
| 8,468,627 | B2 * | 6/2013 | Leach | A47C 20/027 | 5/652 |
| 10,595,652 | B1 * | 3/2020 | Winer | G06V 40/103 | |
| 10,806,278 | B1 * | 10/2020 | Leach | A47C 20/025 | |
| 10,973,346 | B1 * | 4/2021 | Winer | A47G 9/1036 | |
| 11,051,629 | B1 * | 7/2021 | Leach | A47C 20/021 | |
| 11,678,752 | B2 * | 6/2023 | Baumel | A61G 7/07 | 5/636 |
| D1,043,184 | S * | 9/2024 | Yarlagadda | D6/601 | |
| 2004/0117015 | A1 * | 6/2004 | Biscup | A61F 2/4465 | 623/16.11 |
| 2004/0168329 | A1 * | 9/2004 | Ishimaru | A43D 1/025 | 33/3 R |
| 2004/0260402 | A1 * | 12/2004 | Baldini | A61F 2/80 | 623/36 |
| 2005/0022305 | A1 * | 2/2005 | Bieganek | A61G 5/1043 | 5/652 |
| 2005/0025953 | A1 * | 2/2005 | Hetzel | B29C 33/3878 | 264/222 |
| 2006/0247892 | A1 * | 11/2006 | Peterson | A61B 5/1036 | 702/167 |
| 2009/0153878 | A1 * | 6/2009 | Fujii | G02B 21/0044 | 356/601 |
| 2010/0187888 | A1 * | 7/2010 | Gallegos | A47C 7/029 | 297/452.21 |
| 2012/0305003 | A1 * | 12/2012 | Mark | A61M 16/06 | 703/1 |
| 2015/0111709 | A1 * | 4/2015 | Longfellow | A63B 21/4039 | 482/140 |
| 2016/0110479 | A1 * | 4/2016 | Li | A43D 1/025 | 703/1 |
| 2016/0288439 | A1 * | 10/2016 | Louko | B33Y 10/00 | |
| 2016/0317722 | A1 * | 11/2016 | Miller | A61G 7/07 | |
| 2017/0255185 | A1 * | 9/2017 | Hinshaw | A43D 1/025 | |
| 2019/0022898 | A1 * | 1/2019 | Janssen | B29C 41/38 | |
| 2025/0178269 | A1 * | 6/2025 | Kojima | B29C 55/30 | |
| 2025/0338985 | A1 * | 11/2025 | Nichols | A47G 9/10 | |

* cited by examiner

METHOD OF MANUFACTURING AND USING A PELVIC PILLOW TO ALLEVIATE PRESSURE ON A PERSONS SACRUM

BACKGROUND OF THE INVENTION

This invention relates generally to pelvic pillows and, more particularly, to a method for fabricating a pelvic pillow to represent, match, or conform to the anatomical contour of the sacral or pelvic region of a respective user's body.

Pelvic floor dysfunction affects millions of individuals, leading to discomfort, pain, and a diminished quality of life. Conditions such as pregnancy, postpartum recovery, pelvic organ prolapse, and abdominal surgeries such as a hysterectomy contribute to complications in the pelvic region, often necessitating targeted therapeutic interventions. One of the most effective solutions to alleviate pressure on the sacrum and pelvic floor is the use of a pelvic pillow designed to maintain the pelvis at an optimal incline. However, the effectiveness of such a pillow is significantly enhanced when it is customized to fit the individual's unique anatomy.

During pregnancy and postpartum recovery, the pelvic floor endures substantial strain due to increased weight, hormonal changes, and the birthing process. Standard support cushions may provide some relief but fail to accommodate the specific needs of each individual. A customized pelvic pillow, tailored using a digital scan of the user's sacral anatomy, ensures precise support and pressure distribution. This personalized fit reduces discomfort, enhances circulation, and promotes proper spinal alignment, which is crucial for recovery and long-term pelvic health.

Similarly, individuals suffering from pelvic organ prolapse or those recovering from abdominal surgeries require specialized support to minimize pain and facilitate healing. A generic pillow may not provide the necessary angle or contour to alleviate pressure effectively. A customized pelvic pillow, crafted from foam material and designed to an individual's specifications, optimizes support and prevents further strain on the affected area.

By integrating technology such as digital scanning and advanced fabrication techniques, a personalized pelvic pillow offers a superior alternative to standard cushions. It enhances therapeutic outcomes by ensuring comfort, stability, and targeted relief for individuals dealing with pelvic floor dysfunction.

SUMMARY OF THE INVENTION

Accordingly, a method for alleviating pressure on a person's sacrum involves the provision of a pelvic pillow that is specifically tailored to the sacrum of the person. A pelvic pillow according to the present invention will include at least an inclined upper surface configured to elevate the patient's pelvis to a predetermined angle, the inclined surface having a thicker end that, in use, is positioned toward the patient's feet and a thinner end positioned toward the patient's head. The inventive method includes steps for customizing the pelvic pillow to a respective user, namely, including providing a moldable material to the user with instructions for the patient to apply pressure to the moldable material while lying in a supine position so as to create a mold representing the sacral region of the user's body. A method for customizing the pelvic pillow may include scanning the created mold to generate a digital file representative of the sacral contour and using the digital file to fabricate the pelvic pillow from a foam material.

Therefore, a general object of this invention is to provide a customized pelvic pillow, as aforesaid, for alleviating pressure on a person's sacrum.

Another object of this invention is to provide a pelvic pillow having an upper surface that defines an angle of incline that is associated with and representative of a respective user's sacrum or pelvic floor.

Still another object of this invention is to provide a customized pelvic pillow, as aforesaid, that provides phenolic material to a respective user by which to create a mold of the respective user's sacrum.

Yet another object of this invention is to provide a customized pelvic pillow, as aforesaid, that includes scanning the created mold and generating a representative digital file that is then used to fabricate the pelvic pillow.

Other objects and advantages of the present invention will become apparent from the following description taken in connection with the accompanying drawings, wherein is set forth by way of illustration and example, embodiments of this invention.

DESCRIPTION OF THE PREFERRED EMBODIMENT

A method for manufacturing and using a pelvic pillow according to a preferred embodiment of the present invention will now be described with reference to the accompanying drawings. The method 100 includes providing a pelvic pillow 10 having an inclined upper surface 14 that is representative of a sacral region of a respective user.

A pelvic pillow 10 that alleviates pressure on a respective user's sacrum may be fabricated from a foam material using specific method steps that will be discussed later in more detail. For the sake of clarity, it will be understood that the respective user of the pelvic pillow 10 may be referred to as a user, a patient, or a person. It is further understood that use of the pelvic pillow 10 may occur in a hospital or clinic environment or in a user's own home so long as the user is lying face up on the pelvic pillow and the pelvic pillow is adjusted as described below.

Figure 1:
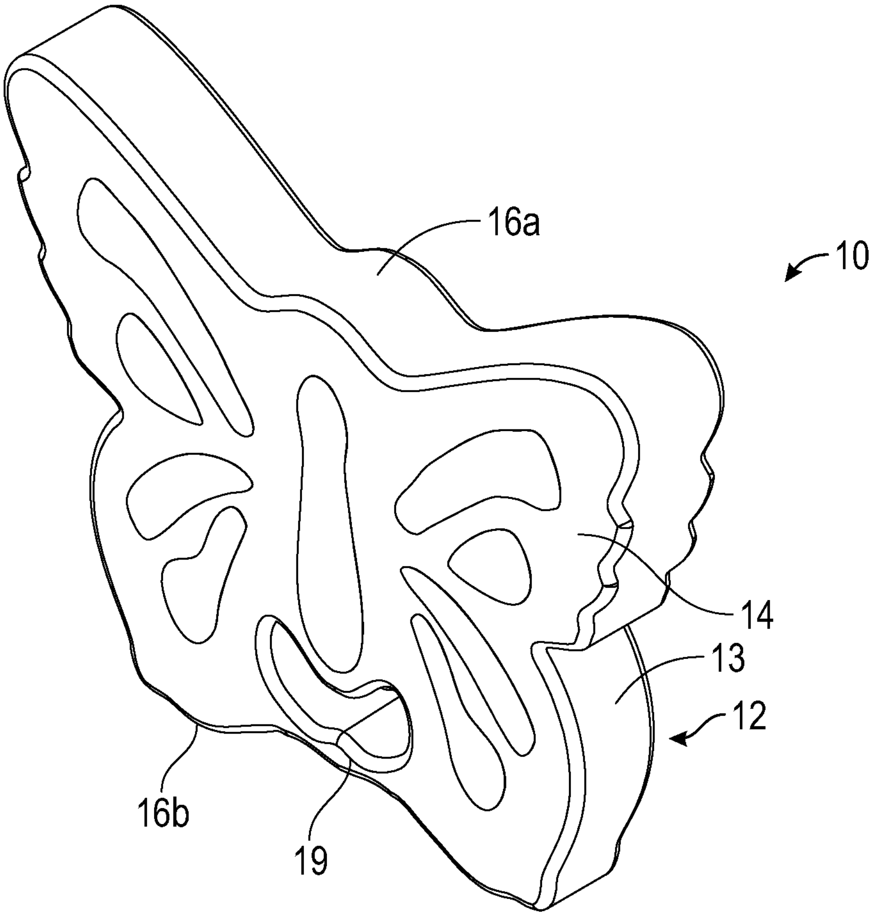
FIG. 1 is a perspective view of a customized pelvic pillow generated according to the present invention.
Figure 2A:
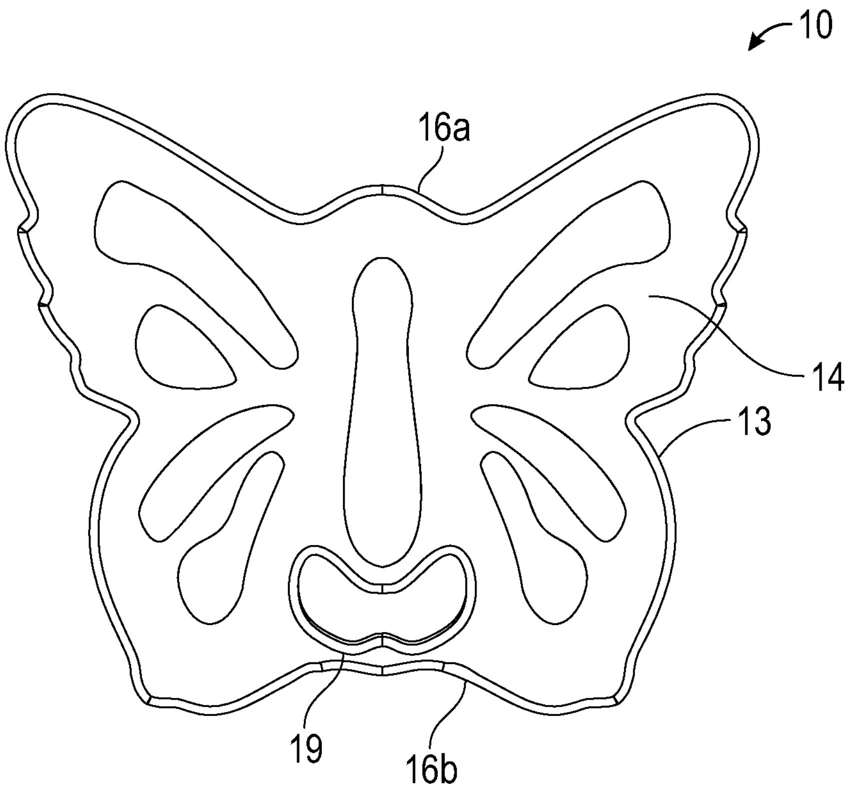
FIG. 2*a* is top view of the customized pelvic pillow as in claim 1.
Figure 2B:
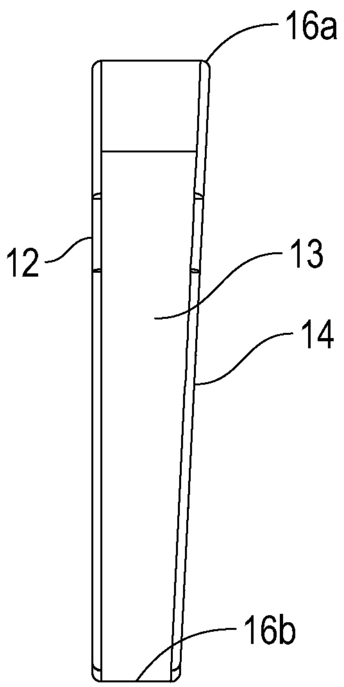
FIG. 2*b* is a side view of the pelvic pillow as in FIG. 2*a;*

As illustrated in FIG. 1, the pelvic pillow 10 may include a bottom surface 12 upon which the pillow may be supported on the level service of a mattress (such as a user's bed) and may include a continuous sidewall 13 extending upwardly from the bottom surface The pelvic pillow 10 includes an inclined upper surface 14 situated atop upper edges of the sidewall 13, the upper surface 14 defining an angle or slope between opposed ends. The upper surface 14 may be angled or offset relative to an imaginary horizontal plane such as that defined by the bottom surface 12. The inclined upper surface 14 correctly implies that the pelvic pillow 10 has a "thicker" end 16*a* and a "thinner" end 16*b* (which may also be described as having a thicker edge and a thinner edge). It is understood that the pelvic pillow 10 may include a respective size dimension appropriate for the size of the user, such as an adult size versus a child size. In any case, the pelvic pillow 10 defines a surface area sufficiently large to be positioned and adjusted beneath the sacral or pelvic region of a respective user lying in a supine orientation. As will be described again regarding a preferred usage, the thicker end 16*a* is positioned in the direction of a user's feet and the thinner end 16*b* is positioned in the direction of a user's head FIGS. 1 and 4A to 4C.

Figure 4A:
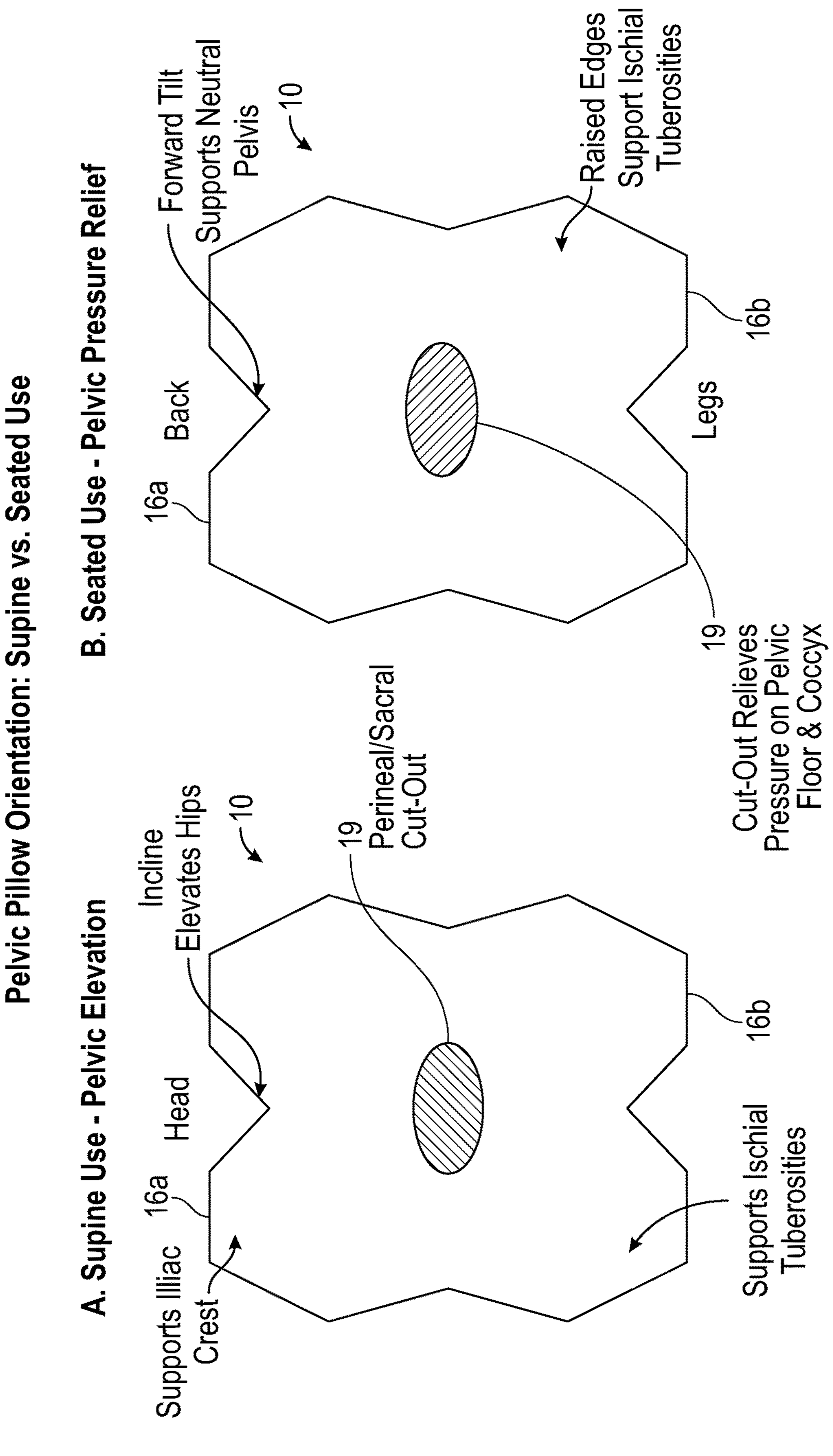
FIG. 4A is a diagram illustrating the customized pelvic pillow as in FIG. 1, illustrating that pelvic pillow may be used by a patient in either a seated or supine orientation.

When positioned and adjusted properly, the pelvic pillow 10 is a weight distribution and circulation-enhancing structure that minimizes pressure on a user's sacrum by distributing weight across the user's entire pelvic area. In an embodiment, the upper surface 14 may define a cut out 19 area that is inset or a depression and configured for receiving a user's sacrum or tailbone region (FIG. 4*a*). It is understood that the cut out 19 helps to stabilize the pelvic pillow 10 when reclined upon by a user. In addition, the cut out 19 area may have a configuration that is identical or substantially similar to a user's sacrum and tailbone and therefore contribute to comfort and healing (FIG. 4*a*). In respective embodiments, the pelvic pillow 10 may provide relief to a user in a seated orientation or in a supine/reclined orientation.

Figure 3:
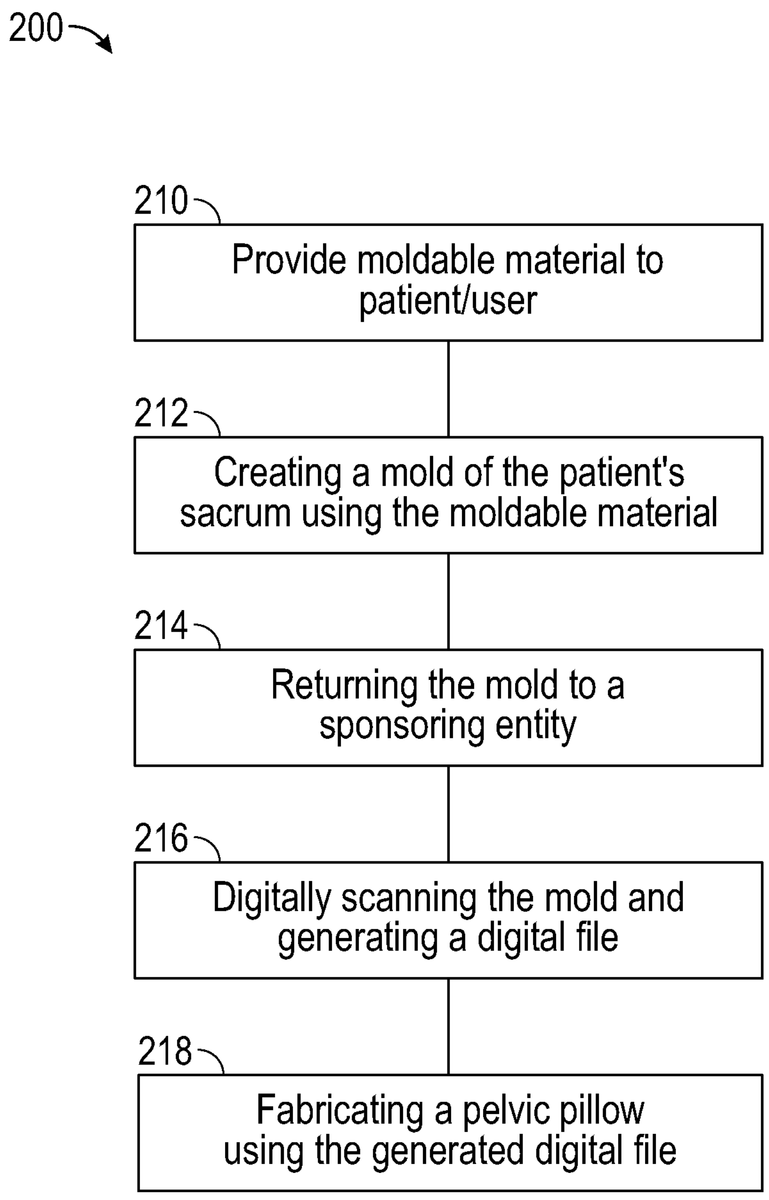
FIG. 3 is a flowchart illustrating the method for alleviating pressure on a person's sacrum by generating a customized pelvic pillow according to the present invention.

To enhance or maximize the benefits of a pelvic pillow, the pelvic pillow 10 should be constructed to be anatomically identical or closely-similar to the sacral region 100 of a respective user's body. A method 200 for customizing the manufacturing of the pelvic pillow 10 is illustrated in FIG. 3. Accordingly, the present invention includes a method step 210 of providing a moldable material to a person or patient to whom a pelvic pillow 10 will be constructed. Stated another way, a sponsoring agency or company implementing the present invention may deliver a mold submission kit to a user along with instructions that will enable the user to create a mold 212 of the patient's sacrum. For instance, the user may be supplied with a moldable material such as a phenolic material with instructions to lie thereon in a supine position and to apply pressure on the moldable material. Accordingly, a mold is created 212 at the user's sacrum 100 that pelvic region. Preferably, the created mold is returned to the sponsoring agency or company.

A phenolic material is a type of thermoset resin typically formed by polymerizing phenol with formaldehyde in the presence of a catalyst, the resulting material then being reinforced or enhanced with substances like paper, cotton fiber, fiberglass, or other fillers to create a durable, heat-resistant, and chemically resistant phenolic laminate or composite material. The phenolic material is configured to hold the shape of an object that is pressed against it, at least for a reasonable amount of time. Indeed, impregnating layers of the phenolic material with paper, cloth, or glass fabric reduces the natural brittleness and degradability of the phenolic material—making phenolic material a good candidate to receive the mold of a user's sacral region after which it is returned to the agency or company for fabrication. One such phenolic material is known as Bakelite. There are other moldable materials that might also be suitable, such as materials that include polycarbonate, epoxy, and the like.

According to the inventive method 200 (FIG. 3), the created mold may be returned (step 214) to a sponsoring agency or company where the mold may be scanned so as to generate a digital file (step 216). The type of scanner or scanning methodology will determine the type of digital file that is generated which will also affect the method or hardware used for fabricating the pelvic pillow 10. There are multiple methods for scanning that will be described below. In an embodiment, a structured light scanner may be utilized and that projects a pattern of light onto the phenolic mold. The structured light scanner may include a camera that captures distortions in the pattern to reconstruct a high-resolution 3D model. The deformation of the projected pattern contains valuable information about the object's shape and depth. By analyzing the distortions in the pattern, sophisticated algorithms reconstruct a highly accurate 3D model of the object. This process is known as triangulation, where the scanner calculates the position of each point on the object's surface by comparing the angles and positions of the projected pattern in the images captured by the camera. Then, the 3D model is exported as a CAD file for some fabrication, whether by CNC milling or 3D printing using film materials.

In another embodiment, the created mold may be scanned 216 using a handheld or stationary laser scanner which captures the geometry and texture of the mold and creates a point cloud that is then converted into a 3D surface model. The 3D model may be used in the machining rather fabrication (step 218) of the pelvic pillow 10. Stated another way, the laser scanner emits a beam of infrared laser light onto a rotating mirror that effectively paints the surrounding environment with light. The scanner head rotates, sweeping the laser across the object or area. Objects in the path of the laser reflect the beam back to the scanner, providing the geometry that is interpreted into 3D data.

In yet another embodiment, the created mold may be scanned 216 using an industrial CT scanner that takes several images and stitches them together into a 3D digital mesh. The digital model is converted into a toolpath appropriate for CNC milling or additive manufacturing. Industrial CT scanning uses X-rays to create detailed 3D models of objects by capturing numerous 2D images as the object rotates, which are then reconstructed into a 3D volume using computer algorithms.

Once the created mold 212 (such as using the phenolic material) has been scanned 216 and the corresponding digital model has been generated, the inventive method according to the present invention calls for actual fabrication 218 of a pelvic pillow 10. As described briefly above, the digital file may be used for CNC machining to carve the pelvic pillow 10 from a block of foam material. Alternately, the file may be converted to a 3D-printable mold for urethane or memory foam casting.

Figure 4B:
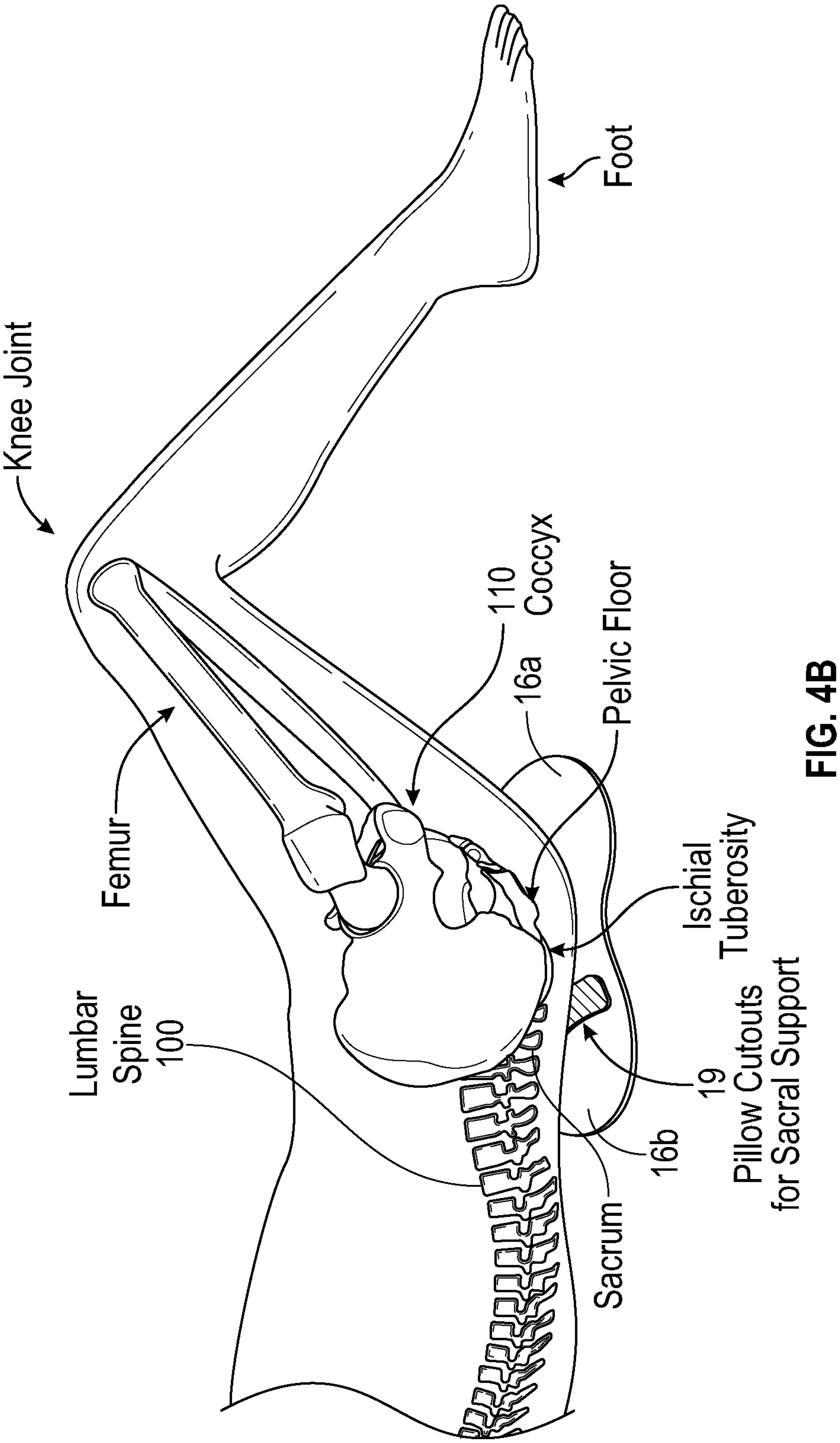
FIG. 4B is an anatomical diagram illustrating a person's pelvic region when in a supine orientation and in communication with the pelvic pillow according to the present invention.
Figure 4C:
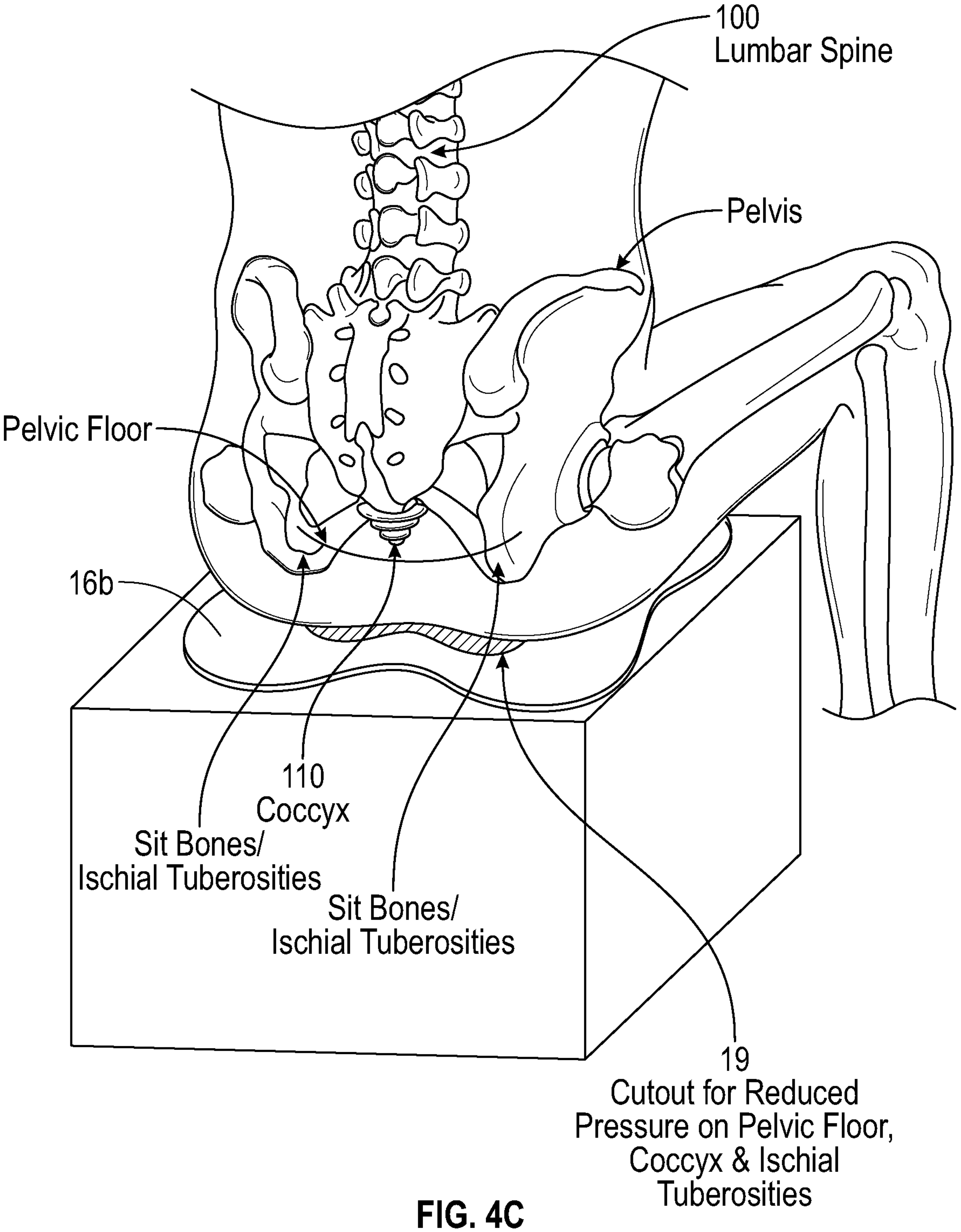
FIG. 4C is another and topical diagram illustrating a person's pelvic region when in a seated position in communication with the pelvic pillow according to the present invention.

In use, a person who has pain or discomfort in the sacral or pelvic region may desire treatment or otherwise seek relief from a vendor who is implementing the present invention. Accordingly, the patient in need of treatment may request or the propose that a custom-tailored pelvic pillow 10 be constructed with dimensions that are specifically and anatomically designed to fit the respective user. More particularly, the user may be provided with the moldable material 210, such as a phenolic material, along with instructions to create a mold of the user's sacrum by lying in a supine position and applying pressure to the moldable material (step 212). Further, the "customer/client" will be instructed to return the created mold (step 214) which will be scanned (step 216) as described above and the pelvic pillow 10 will be fabricated (step 218). Accordingly, the customized pelvic pillow 10 may be positioned, the user's posture adjusted if necessary, and maintained in use for a predetermined time to alleviate pressure on the sacrum and to improve blood circulation of the customer/client. For best results, the user will position his sacral region 100 and, more particularly, his tailbone 110 into the recessed cutout 19 area of the pelvic pillow 10. The user lying in a supine position atop the pillow 10 and oriented such that his tailbone 110 is received ny and aligned with said cutout 19 is illustrated in FIG. 4B.

It is understood that while certain forms of this invention have been illustrated and described, it is not limited thereto except insofar as such limitations are included in the following claims and allowable functional equivalents thereof.

What is claimed is:

1. A method for manufacturing a pelvic pillow that alleviates pressure on a patient's sacrum, the method comprising:

providing a moldable material to a patient;

instructing the patient to create a mold of patient's sacrum by lying in a supine position and applying pressure to the moldable material only over the patient's sacral region while lying in a supine position so as to create a negative impression of the patient sacral anatomy in the molded material;

receiving the negative impression from the patient;

digitally scanning the negative impression to generate a digital three-dimensional model representative of the patient sacral anatomy;

fabricating a pelvic pillow from a foam material using the digital three-dimensional model;

wherein the pelvic pillow is customized according to the sacral contour of the patient and comprises:

an inclined upper surface configured to elevate the patient's pelvis to a predetermined angle;

a thicker end positioned toward the patient's feet and a thinner end positioned toward the patient's head; and a recessed sacral receiving region formed in the inclined upper surface and having a contour anatomically corresponding to the patient's sacral anatomy represented by the digital three-dimensional model;

wherein the recessed sacral receiving region comprises a positive anatomical reproduction of at least a portion of the patient's sacral anatomy represented by the digital three-dimensional model wherein the recessed sacral receiving region is configured to receive the same patient's sacrum from which the negative impression was obtained; and wherein the recessed sacral receiving region reduces localized pressure on the patient's sacrum while distributing body weight across surrounding pelvic tissue.

2. The method as in claim 1, wherein said moldable material is phenolic material.

3. The method as in claim 2, wherein said phenolic material is reinforced with paper, cotton fabric, or fiberglass, so as to create a durable, heat-resistant, and chemically resistant phenolic laminate or composite material.

4. The method as in claim 3 wherein said phenolic material is a thermosetting resin known as Bakelite.

5. The method as in claim 1, wherein said moldable material includes polycarbonate or epoxy.

6. The method as in claim 1, wherein said upper surface defines a cutout that is configured to receive the patient's sacrum.

7. The method as in claim 1, wherein said step of digitally scanning the created mold to generate a digital file representative of the sacral contour includes using a structured light scanner to project a pattern of light onto the created mold, and said light scanner having a camera configured to capture distortions in the pattern to construct a high-resolution 3D model file.

8. The method as in claim 1, wherein said step of digitally scanning the created mold to generate a digital file representative of the sacral contour includes using a laser scanner to scan the created mold, said laser scanner be configured to capture a geometry and texture of the created mold and converting said captured geometry into a 3D model file.

9. The method as in claim 1, wherein said step of digitally scanning the created mold to generate a digital file representative of the sacral contour includes using computed tomography (CT) scanning that is configured to generate a toolpath for CNC milling.

10. The method as in claim 1, wherein the foam material is selected from a group consisting of memory foam, polyurethane foam, and viscoelastic foam.

11. The method as in claim 1, wherein the upper surface defines a slope between 10 and 30 relative to an imaginary horizontal plane.

12. The method as in claim 4, wherein the moldable phenolic material hardens upon exposure to air to retain the sacral contour of the patient.

* * * * *